(12) United States Patent
Shinden

(10) Patent No.: US 7,109,491 B2
(45) Date of Patent: Sep. 19, 2006

(54) RADIATION IMAGE DETECTOR AND RADIATION IMAGE GENERATING SYSTEM

(75) Inventor: Yuko Shinden, Hachioji (JP)

(73) Assignee: Konica Minolta Medical & Graphic Inc., Tokyo (JP)

( * ) Notice: Subject to any disclaimer, the term of this patent is extended or adjusted under 35 U.S.C. 154(b) by 0 days.

(21) Appl. No.: 11/093,811

(22) Filed: Mar. 29, 2005

(65) Prior Publication Data

US 2006/0169907 A1   Aug. 3, 2006

(30) Foreign Application Priority Data

Jan. 31, 2005   (JP) ............................. 2005-023823

(51) Int. Cl.
*G01T 1/24*   (2006.01)
(52) U.S. Cl. ............................. 250/370.09; 250/370.11
(58) Field of Classification Search .......... 250/370.09, 250/370.11
See application file for complete search history.

(56) References Cited

U.S. PATENT DOCUMENTS

| 5,122,665 | A | * | 6/1992 | Kurashima | 250/590 |
| 5,331,179 | A | * | 7/1994 | Lee et al. | 250/591 |
| 5,748,340 | A | * | 5/1998 | Shimizu | 358/482 |
| 5,773,832 | A | * | 6/1998 | Sayed et al. | 250/370.09 |
| 6,539,076 | B1 | * | 3/2003 | Shoji | 378/98.8 |
| 2002/0017610 | A1 | * | 2/2002 | Takemoto | 250/370.09 |
| 2002/0044211 | A1 | * | 4/2002 | Tujii et al. | 348/302 |
| 2002/0053650 | A1 | * | 5/2002 | Iwakiri | 250/588 |
| 2003/0042418 | A1 | * | 3/2003 | Yamamoto | 250/336.1 |
| 2004/0079908 | A1 | * | 4/2004 | Ohkubo | 250/582 |

* cited by examiner

*Primary Examiner*—David Porta
*Assistant Examiner*—Mark R. Gaworecki
(74) *Attorney, Agent, or Firm*—Frishauf, Holtz, Goodman & Chick, P.C.

(57) ABSTRACT

A radiation image detector for detecting an irradiated radiation and for obtaining radiation image information, includes: an image generation mode; and a plurality of image generation standby modes, wherein the plurality of image generation standby modes includes: a first standby mode having electric power consumption amount at least lower than electric power consumption amount of the image generation mode; and a second standby mode having electric power consumption amount lower than the electric power consumption amount of the first standby mode, and the radiation image detector includes a switching section for switching among the image generation mode and the plurality of image generation standby modes.

9 Claims, 11 Drawing Sheets

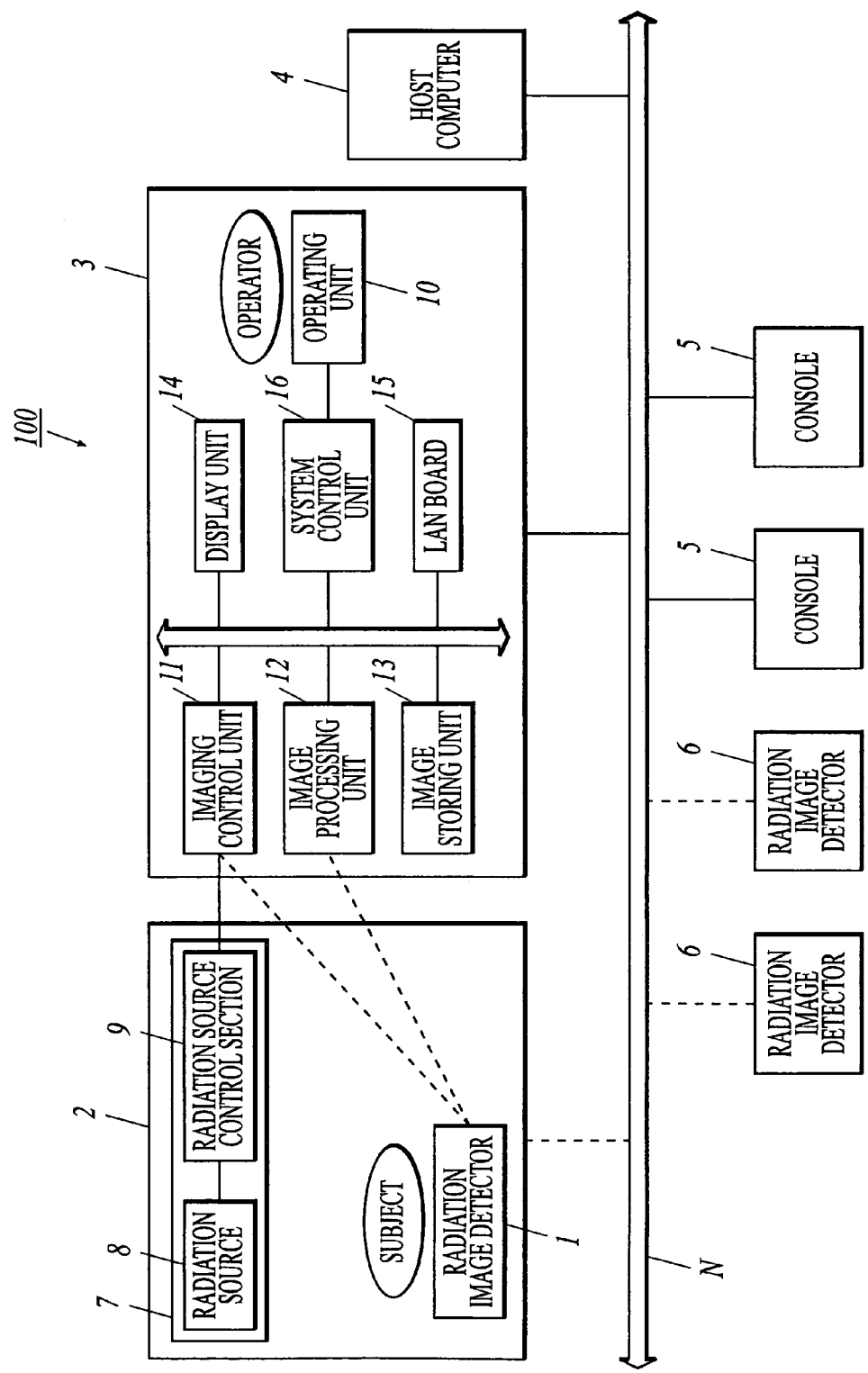

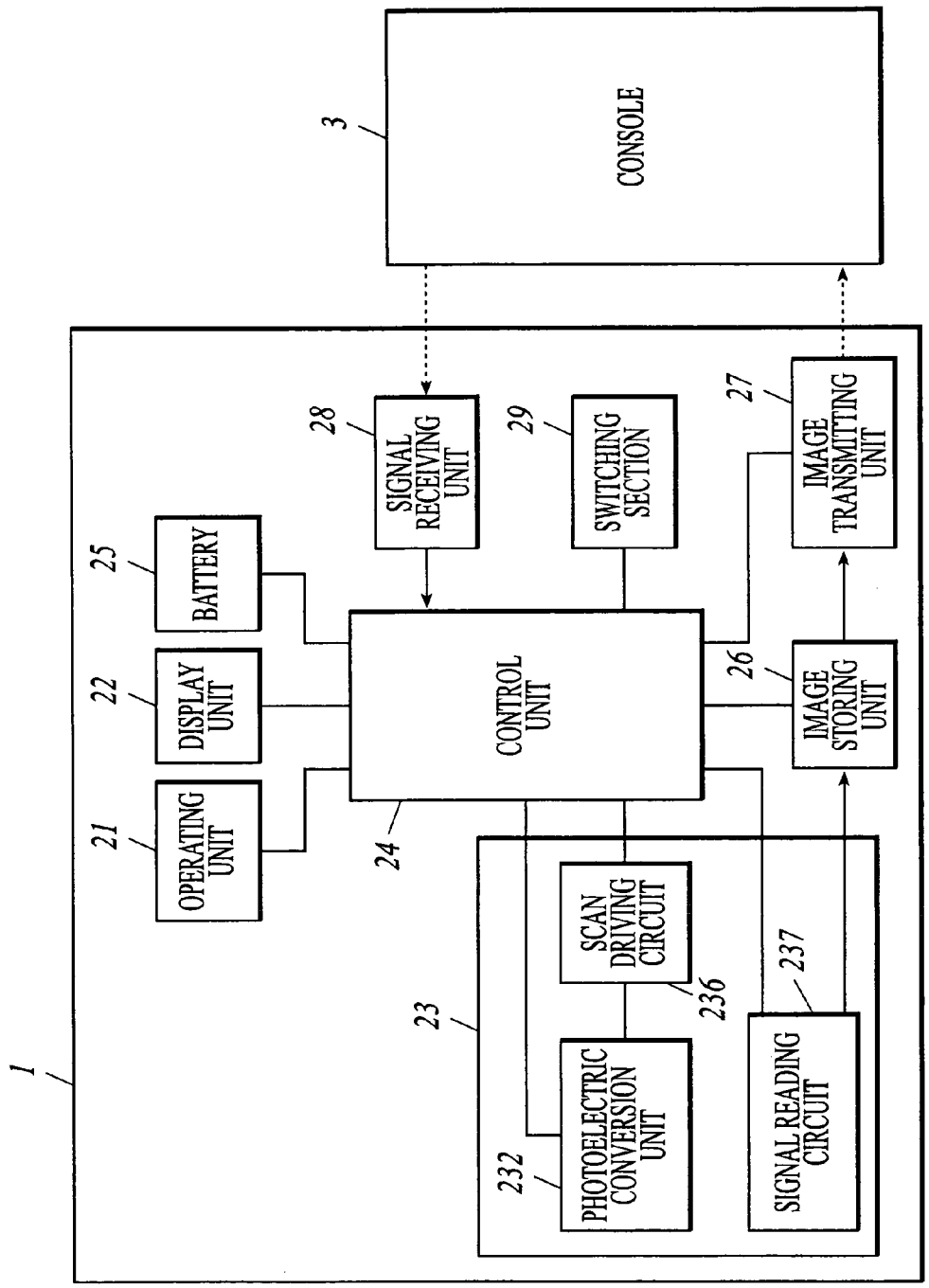

FIG.6

| | SECOND STANDBY MODE | FIRST STANDBY MODE | INITIALIZATION | X-RAY IRRADIATION | READING | IMAGE SIGNAL TRANSMITTANCE | FIRST STANDBY MODE | SECOND STANDBY MODE |
|---|---|---|---|---|---|---|---|---|
| SIGNAL READING CIRCUIT | | | | | | | | |
| SCAN DRIVING CIRCUIT | | | | | | | | |
| PD | | | | | | | | |
| TFT | | | | | | | | |
| IMAGE STORING UNIT | | | | | | | | |
| IMAGE TRANSMITTING UNIT | | | | | | | | |
| SIGNAL RECEIVING UNIT | | | | | | | | |
| ELECTRIC POWER CONSUMPTION | | | | | | | | |

FIG. 8

| | SECOND STANDBY MODE | FIRST STANDBY MODE | INITIALIZATION | X-RAY IRRADIATION | READING | IMAGE SIGNAL TRANSMITTANCE | FIRST STANDBY MODE | SECOND STANDBY MODE |
|---|---|---|---|---|---|---|---|---|
| SIGNAL READING CIRCUIT | | | | | | | | |
| SCAN DRIVING CIRCUIT | | | | | | | | |
| PD | | | | | | | | |
| TFT | | | | | | | | |
| IMAGE STORING UNIT | | | | | | | | |
| IMAGE TRANSMITTING UNIT | | | | | | | | |
| SIGNAL RECEIVING UNIT | | | | | | | | |
| ELECTRIC POWER CONSUMPTION | | | | | | | | |

FIG.9

| | SECOND STANDBY MODE | FIRST STANDBY MODE | INITIALIZATION | X-RAY IRRADIATION | READING | IMAGE SIGNAL TRANSMITTANCE | FIRST STANDBY MODE | SECOND STANDBY MODE |
|---|---|---|---|---|---|---|---|---|
| SIGNAL READING CIRCUIT | | | | | | | | |
| SCAN DRIVING CIRCUIT | | | | | | | | |
| PD | | | | | | | | |
| TFT | | | | | | | | |
| IMAGE STORING UNIT | | | | | | | | |
| IMAGE TRANSMITTING UNIT | | | | | | | | |
| SIGNAL RECEIVING UNIT | | | | | | | | |
| ELECTRIC POWER CONSUMPTION | | | | | | | | |

FIG.10

| | THIRD STANDBY MODE | SECOND STANDBY MODE | FIRST STANDBY MODE | INITIALIZATION | X-RAY IRRADIATION | READING | IMAGE SIGNAL TRANSMITTANCE | FIRST STANDBY MODE | SECOND STANDBY MODE | THIRD STANDBY MODE |
|---|---|---|---|---|---|---|---|---|---|---|
| SIGNAL READING CIRCUIT | | | | | | | | | | |
| SCAN DRIVING CIRCUIT | | | | | | | | | | |
| PD | | | | | | | | | | |
| TFT | | | | | | | | | | |
| IMAGE STORING UNIT | | | | | | | | | | |
| IMAGE TRANSMITTING UNIT | | | | | | | | | | |
| SIGNAL RECEIVING UNIT | | | | | | | | | | |
| ELECTRIC POWER CONSUMPTION | | | | | | | | | | |

FIG.11

| | THIRD STANDBY MODE | FIRST STANDBY MODE | INITIALIZATION | X-RAY IRRADIATION | READING | IMAGE SIGNAL TRANSMITTANCE | FIRST STANDBY MODE | SECOND STANDBY MODE | THIRD STANDBY MODE |
|---|---|---|---|---|---|---|---|---|---|
| SIGNAL READING CIRCUIT | | | | | | | | | |
| SCAN DRIVING CIRCUIT | | | | | | | | | |
| PD | | | | | | | | | |
| TFT | | | | | | | | | |
| IMAGE STORING UNIT | | | | | | | | | |
| IMAGE TRANSMITTING UNIT | | | | | | | | | |
| SIGNAL RECEIVING UNIT | | | | | | | | | |
| ELECTRIC POWER CONSUMPTION | | | | | | | | | |

RADIATION IMAGE DETECTOR AND RADIATION IMAGE GENERATING SYSTEM

BACKGROUND OF THE INVENTION

1. Field of the Invention

The present invention relates to a radiation image detector and a radiation image generating system. In particular, the present invention relates to a radiation image detector and a radiation image generating system each of which is capable of generating an image quickly, saving electric power and realizing a long life duration thereof.

2. Description of Related Art

So far, for a medical diagnosis, a radiation image obtained by irradiating a radiation such as X-ray or the like to a subject and by detecting an intensity distribution of the radiation transmitted through the subject has been widely used. Recently, what has been proposed is a radiation image generating system using an FPD (Flat Panel Detector), which, at the time of generating an image, detects a radiation, converts the detected radiation into electrical signals and accumulates the electrical signals as radiation image information.

What is known as the radiation image generating system, for the purpose of improving flexibility of a system structure, is a system comprising an FPD placed in an image generating room and a predetermined console such as PC (Personal Computer) or the like for performing an image processing, wherein the PC and the FPD are connected through a predetermined communication line (see JP-Tokukai-2003-199726A).

Furthermore, what has been proposed is a system comprising a cassette-type FPD and a console wherein the cassette-type FPD and the console are each other capable of transmitting/receiving various information such as radiation image information or the like, according to a wireless system (for example, see JP-Tokukai-2003-210444A). In the cassette-type FPD, the FPD is contained in a cassette. Therefore, transportability and handling convenience of the FPD are improved, and further flexibility of the system structure is improved.

In view of flexibility improvement, the fact that the cassette-type FPD does not have an obstacle wiring can be cited as one of the characteristics. In this case, the cassette-type FPD incorporates therein a battery charger as an electric power supply source. When the battery charger is consumed to exhaustion of the electric power, the FPD is reused after either charging is performed or a battery is changed.

Therefore, when the electric power is exhausted according to a condition of use or the like, charging needs to be done lots of times in a day, and therefore it is very inconvenient. Further, if the electric power is exhausted when an image is necessary to be generated, what occurs is an inconvenience of not being capable of performing the image generation immediately. Alternatively, when the electric power is exhausted during an image generation, the image generation has to be re-performed. Therefore, there is a possibility of increasing a danger of exposure to the subject. Accordingly, development of a cassette-type FPD which is lightweight and can remain usable for a long time has been necessitated.

Therefore, reduction of wasteful electric power consumption when used has been attempted conventionally. Normally, in an FPD, a power of the radiation image detector is turned on at the beginning of the day, and except for the time of image generation, the FPD is on standby under an image generation standby mode where a voltage is being applied to all the portions that will function after an image is generated, and the power is turned off after the FPD is operated for a whole day so as to be capable of immediately starting generating of an image of a patient except for the time of image generation. At this time, in the FPD, switching between an image generation mode under which image generation is actually performed and the image generation standby mode under which image generation is not actually performed but electric power consumption is smaller than that of the image generation mode and it is possible to immediately start up the FPD to the image generation mode is done, where the switching of each mode is done by attaching/detaching an adapter included in the FPD, as described in JP-Tokukai-2004-141473A. Alternatively, the switching is done by a switch and a timer provided with the FPD as described in JP-Tokukaihei-9-294229A.

As a result, under the standby state where the FPD is not used for image generation, electric power consumption is reduced by not applying a voltage to components to which it is not necessary to apply the voltage on standby, and a time period which is from turning on the power to reaching the state where it is possible to actually perform the image formation, that is, the image generation mode, is reduced. Thereby, electric power saving of the FPD by reducing electric power consumption under the image generation standby mode and immediate transition to the image generation mode have been realized.

However, although electric power consumption amount under the conventional image generation standby mode is smaller than that of the image generation mode, the electric power consumption amount under the conventional image generation standby mode is still larger than that of a state where the power is entirely off. It is very uneconomical especially when only few times of image generation are performed in a day, and therefore it is not sufficient to regard the conventional art as electric power saving.

Further, in order to switch the FPD to the image generation mode immediately, a voltage is for a long time applied to many of the components of the FPD. Thereby, the PD, a TFT and the like are deteriorated, and their sensitivities are decreased. As a result, a life duration of the FPD is shortened despite the fact that the FPD is not actually used very frequently for image generation.

In this way, under the conventional image generation standby mode, it was not possible to realize all of: the immediate transition to the image generation mode; the electric power saving; and the realization of a long life duration, at the same time.

SUMMARY OF THE INVENTION

An object of the present invention is to a radiation image detector and a radiation image generating system capable of realizing immediate switching of the radiation image detector to an image generation mode and reducing electric power consumption under an image generation standby mode even more, for realizing electric power saving and realizing a long life duration thereof.

In accordance with a first aspect of the present invention, a radiation image detector for detecting an irradiated radiation and for obtaining radiation image information, comprises: an image generation mode; and a plurality of image generation standby modes, wherein the plurality of image generation standby modes comprises: a first standby mode having electric power consumption amount at least lower than electric power consumption amount of the image generation mode; and a second standby mode having electric power consumption amount lower than the electric power consumption amount of the first standby mode, and the radiation image detector comprises a switching section for switching among the image generation mode and the plurality of image generation standby modes.

According to the detector of the first aspect, the detector comprises a plurality of image generation standby modes having lower electric power consumption amount than the image generation mode, at least two of the plurality of image generation standby modes have different electric power consumption amount from each other, and the switching section switches among the image generation mode and the plurality of image generation standby modes according to a status of use. Therefore, it is possible to reduce the electric power consumption under the image generation standby mode, and realize power saving and a long life duration of the detector, compared to a case of switching between one image generation standby mode and the image generation mode. In particular, when the detector is set to a state where the first standby mode can be immediately switched to the image generation mode, while the mode is immediately switched to the image generation mode, it is possible to further reduce electric power consumption under the image generation standby mode, and realize electric power saving and a long life duration of the detector.

Preferably, the detector of the first aspect further comprises: a signal reading circuit; a scan driving circuit; a photoelectric conversion unit; an image storing unit; an image transmitting unit; and a signal receiving unit, wherein the switching section does not apply a voltage to at least the signal reading circuit under the first standby mode.

According to the above-mentioned detector, under the first standby mode, a mode is switched among the image generation mode and the plurality of image generation standby modes so as not to apply a voltage to the signal reading circuit, which requires the most amount of electric power consumption amount. Therefore, it is possible to switch from the first standby mode to the image generation mode immediately, and compared to a case of not applying a voltage to other components, it is possible to reduce large amount of electric power consumption under the first standby mode.

Preferably, in the detector of the first aspect, the switching section does not apply a voltage to at least the photoelectric conversion unit under the second standby mode.

According to the above-mentioned detector, a mode is switched among the image generation mode and the plurality of image generation standby modes under the second standby mode so as not to apply a voltage to the photoelectric conversion unit. Therefore, under the second standby mode, by not applying a voltage to the photoelectric conversion unit, it is possible to reduce electric power consumption amount, and also it is possible to prevent the photoelectric conversion unit from being deteriorated due to long unnecessary voltage applying time, and thereby it is possible to prevent a life duration of the detector from being shortened.

Preferably, in the detector of the first aspect, the switching section switches among the image generation mode and the plurality of image generation standby modes, according to one of: a signal from a mechanical switch; a signal from outside; and a signal from a sensor.

According to the above-mentioned detector, the switching section is capable of switching among the image generation mode and the plurality of image generation standby modes based on a detection of one of: a signal from a mechanical switch; a signal from outside such as a console or the like; and a signal from a sensor. Therefore, it is possible to switch among the image generation mode and the plurality of image generation standby modes at a suitable timing. Accordingly, it is possible to prevent a voltage from being applied unnecessarily, whereby it is possible to reduce electric power consumption amount and realize a long life duration of the detector.

Preferably, in the detector of the first aspect, the sensor is at least one selected from a group consisting of: an acceleration sensor for detecting a movement; a thermal sensor for detecting heat; an optical sensor for detecting a light; a pressure sensor for detecting a pressure; and an electric sensor for detecting electric energy.

According to the above-mentioned detector, it is possible to switch among the image generation mode and the plurality of image generation standby modes by detecting movement, heat, light, pressure or electric energy. Therefore, it is possible to reduce electric power consumption under the image generation standby mode by detecting movement, heat, light, pressure or electric energy, whereby it is possible to realize electric power saving.

Preferably, the detector of the first aspect further comprises a wireless communication unit for communicating with a wireless signal.

According to the above-mentioned detector, it is possible to transmit/receive various data such as image information and the like to/from an external device connected to the radiation image detector by a wireless signal. Therefore, it is possible to transmit/receive data without cable or the like provided, whereby it is possible to improve flexibility of the system structure.

Preferably, the detector of the first aspect is a cassette type radiation image detector contained in a cassette.

According to the above-mentioned detector, it is not necessary to structure the detector to be integrated with the image generation apparatus and it is possible to make it easy to carry and handle it. Therefore, it is possible to improve flexibility of the system structure.

Preferably, the detector of the first aspect further comprises a battery as an electric power supplying source.

According to the above-mentioned detector, it is possible to have a power source without cable or the like provided. Therefore, it is possible to improve flexibility of the system structure.

In accordance with a second aspect of the present invention, a radiation image generating system comprises: the radiation image detector of the first aspect; and a console for operating the radiation image detector.

According to the system of the second aspect, it is possible to structure a radiation image generating system in which the radiation image detector of the first aspect is operated with the console for obtaining radiation image information. Therefore, it is possible to provide a radiation image generating system in which electric power consumption is reduced under the image generation standby mode and electric power saving is realized.

BRIEF DESCRIPTION OF THE DRAWINGS

The present invention will become more fully understood from the detailed description given hereinafter and the accompanying drawing given by way of illustration only, and thus are not intended as a definition of the limits of the present inventions and wherein:

FIG. 1 is a schematic block diagram showing a radiation image generating system in a first embodiment of the present invention, FIG. 3 is a control structure diagram showing the radiation image detector when a switching signal is transmitted from a console, FIG. 6 is a view showing a concrete example (pattern 1) of a standby mode, FIG. 8 is a view showing a concrete example (pattern 2) of a standby mode in the second embodiment, FIG. 9 is a view showing a concrete example (pattern 3) of a standby mode in the third embodiment, FIG. 10 is a view showing a concrete example (pattern 4) of a standby mode in the fourth embodiment, and FIG. 11 is a view showing a concrete example (pattern 5) of a standby mode in the fifth embodiment,

PREFERRED EMBODIMENTS OF THE INVENTION

First Embodiment

Figure 2A:
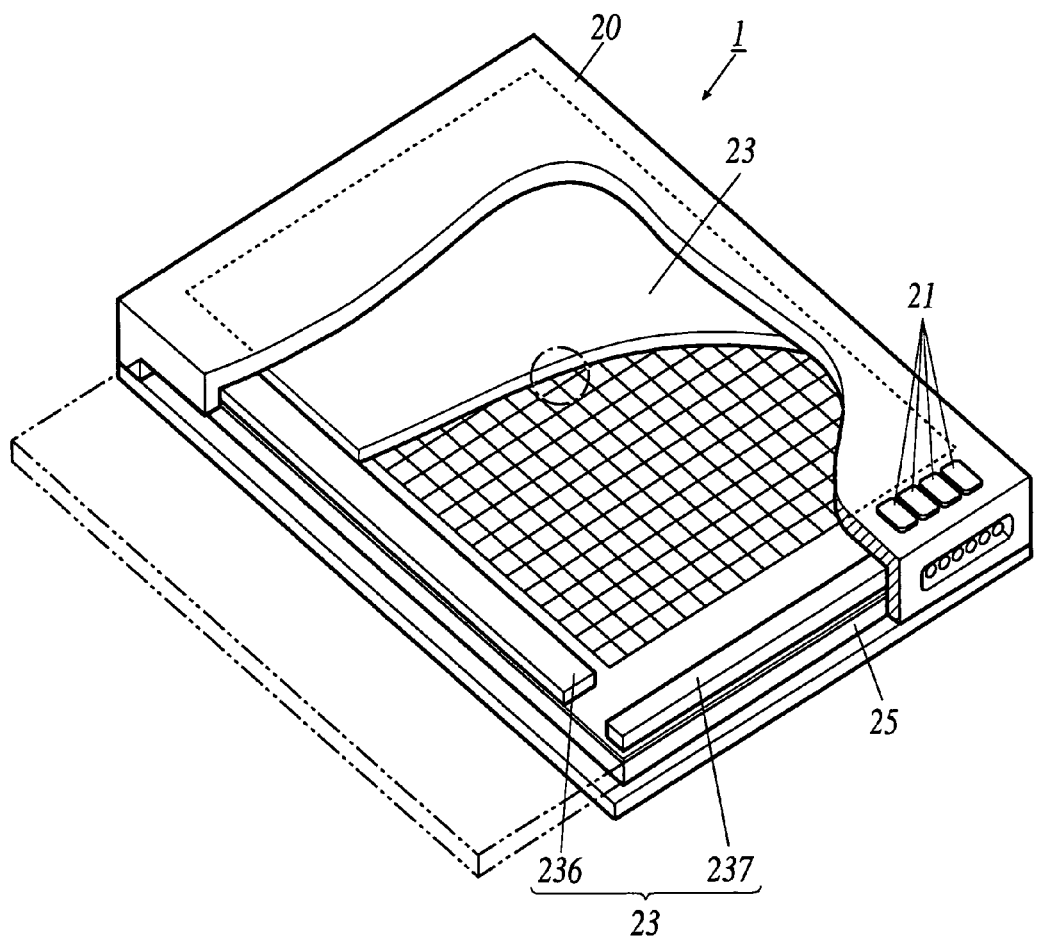
FIG. 2A is a perspective view showing a structure of a radiation image detector.

Hereinafter, embodiments of a radiation image detector and a radiation image generating system in regard to the present invention will be described with reference to drawings. However, the present invention is not limited to represented examples.

FIG. 1 is a schematic block diagram showing the radiation image generating system represented as an embodiment to which the present invention is applied.

As shown in FIG. 1, it is assumed that a radiation image generating system 100 is used for radiation image generation performed in a hospital, and the radiation image generating system 100 comprises: a radiation image generating apparatus 2 placed in an image generation room for example, for performing a radiation image generation by irradiating a radiation such as X-ray or the like to a subject and for obtaining a radiation image at a radiation image detector 1; a console 3 for performing an operation relating to radiation image generation, for displaying the obtained radiation image and for performing an image processing; a host computer 4 for managing reservations of radiation image generation in the hospital and for transmitting an instruction of an image generation request to the console 3 when a predetermined image generation room is reserved for image generation; and a base station (not shown) for performing a communication according to a wireless communication system such as a wireless LAN (Local Area Network) or the like, wherein these apparatuses are connected to each other through a network N. Here, consoles 5, 5 and radiation image detectors 6, 6 in other rooms are connected to the network N, and it is possible to transmit/receive radiation image information obtained at each radiation image detector. Further, the network N may be a communication line dedicated for the system. However, considering the reason such as decrease of flexibility of a system structure or the like, the network N is preferably a preexisting line such as Ethernet (trademark) or the like.

The radiation image generating apparatus 2 comprises a radiation irradiating device 7 and the radiation image detector 1.

The radiation irradiating device 7 is connected to the console 3 through a cable, and comprises a radiation source 8 and a radiation source control section 9. The radiation source control section 9 controls the radiation source 8 according to properties of a radiation to be irradiated (tube voltage applied to the radiation source 8, tube current, irradiation time or the like) instructed from the console 3, to generate a radiation.

The radiation image detector 1 detects a radiation irradiated from the radiation irradiating device 7 and transmitted through a subject S, for obtaining a radiation image. when image generation is performed, the radiation image detector 1 is used to be attached to an image generation platform provided in a radiation irradiating range to which a radiation is irradiated from the radiation source 8, or the like.

The console 3 comprises: an operating unit 10 with which an operator gives an instruction of image generation; an imaging control unit 11 for controlling the radiation irradiating device 7 based on the instruction from the operating unit 10; an image processing unit 12 for applying image processes on image data obtained at the radiation image detector 1, the image processes such as correcting a density or the like; an image storing unit 13 for storing the image data on which the image processing is applied, in a hard disk, a magneto-optical disk or the like; a display unit 14 for displaying an image based on image signals obtained at the radiation image detector 1 in order for the operator to visually confirm whether the image generation has been properly performed; a LAN board 15 for establishing a connection to the network N; and a system control unit 16 for controlling the system of the console 3.

The radiation image detector 1 is a flat panel detector of an indirect type, comprising an emitting layer, a photoelectric conversion layer and a driving circuit, and for detecting a radiation. Hereinafter, with reference to FIG. 2A to FIG. 7, a structure of the radiation image detector 1 will be described.

As shown in FIG. 2A, the radiation image detector 1 comprises a chassis 20 for protecting the inside thereof. The radiation image detector 1 is portably structured as a cassette.

What are provided at the outside of the chassis 20 are: an operating unit 21 for switching an operation of the radiation image detector 1 by a switching operation of the operator; and a display unit 22 (see FIG. 3) for indicating that a preparation for generating a radiation image is completed and that predetermined amount of image signals have been written in an image storing section incorporated therein.

Figure 2B:
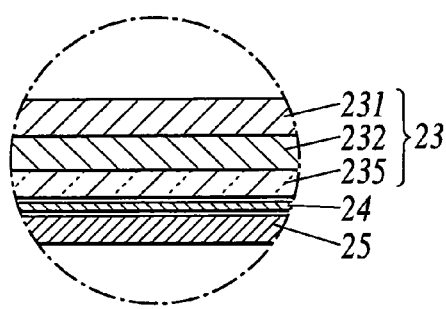
FIG. 2B is a sectional view showing the circled part in the radiation image detector in FIG. 2A.

At the inside of the chassis 20, an imaging panel 23 for converting an irradiated radiation into electrical signals is so formed as to laminate layers. As shown in FIG. 2B, at a side of a radiation irradiating surface of the imaging panel 23, an emission layer 231 for emitting light according to intensity of an incoming radiation is provided. Here, for example, the so-called X-ray, which is an electromagnetic wave transmitting through a material such as a human body, a vessel, an airplane and the like, having wavelength of around 0.1 nm ($1 \times 10^{-10}$ m), is irradiated to the emission layer 231.

The emission layer 231 has a phosphor as a main component, and based on an incoming radiation, the emission layer 231 outputs electromagnetic wave having wavelength from 300 nm to 800 nm, that is, electromagnetic wave (light) from ultraviolet light through visible light to infrared light. In addition, the emission layer 231 is in general called a scintillator layer.

As the phosphor used in the emission layer 231, a phosphor having a parent substance of $CaWO_4$, $CdWO_4$ or the like, or a phosphor having a parent substance of CsI:Tl, $Gd_2O_2S$:Tb, ZnS:Ag or the like in which an emission center substance is activated can be used.

Further, with a rare earth element defined as M, a phosphor represented by a general formula of $(Gd, M, Eu)_2O_3$ can be used.

In particular, it is preferable to use CsI:Tl or $Gd_2O_2S$:Tb because X-ray absorption and emission efficiency is high. By using these types, it is possible to obtain a high quality image having low noise.

What is formed at a surface of an opposite side to the radiation irradiating surface of the emission layer 231, is a photoelectric conversion layer 232 for converting the electromagnetic wave (light) outputted from the emission layer into electrical energy to be accumulated and for outputting image signals based on the accumulated electrical energy.

The photoelectric conversion layer 232 comprises a photoelectric conversion element for generating the electrical energy to be accumulated in each pixel; and a transistor being a switching element for outputting the accumulated electrical energy as signals. Here, the photoelectric conversion layer 232 is not limited to one using the switching element. For example, the photoelectric conversion layer 232 may have a structure of generating and outputting signals corresponding to an energy level of the accumulated electrical energy. In general, the photoelectric conversion layer 232 is formed from amorphous silicon placed on a glass base plate.

As the photoelectric conversion element, for example, a photodiode (PD) 233 is used. However, the photoelectric conversion element is not necessarily limited in particular, and the photoelectric conversion element may be another element such as a solid-state image sensor (charge-coupled device), a photomultiplier or the like.

As the transistor, for example, a thin film transistor (TFT) 234 is used. The TFT 234 may be one using an inorganic semiconductor, which is used for a liquid crystal display and the like, or one using an organic semiconductor.

At a surface of the photoelectric layer 232 of an opposite side to the emission layer 231, a base plate 235 for supporting the emission layer 231 and the photoelectric conversion layer 232 is formed.

On the base plate 235 and at the side of the photoelectric conversion layer 232, a driving circuit is provided. The driving circuit comprises a scan driving circuit 236 for outputting the accumulated electrical energy as image signals; and a signal reading circuit 237 for reading out the accumulated electrical energy according to intensity of the irradiated radiation.

At a surface of the base plate 235 of an opposite side to the photoelectric conversion layer 232, the control unit 24 is provided.

As shown in FIG. 3, the mentioned operating unit 21, the scan driving circuit 236 and the signal reading circuit 237 are connected to the control unit 24. Further, a battery 25, an image storing unit 26, an image transmitting unit 27, a signal receiving unit 28 and a switching section 29, each of which will be described later, are also connected to the control unit 24.

At a surface of the control unit 24 of an opposite side to the base plate 235, the battery 25 having a plate shape is provided as an electric power supply source for supplying electric power to each component structuring the radiation image detector 1. Such a configuration makes it possible to make the radiation image detector 1 thin. For example, a primary battery such as a manganese battery, a nickel-cadmium battery, a mercury battery, a lead battery and the like, a rechargeable secondary battery are applied to the battery 25. In addition, the battery 25 has a thin shape and is exchangeable by taking the battery 25 out from a side part of the chassis 20.

And so forth, at the inside of the chassis 20, the image storing unit 26 as an image storing section for storing the image signals outputted from the imaging panel 23 by using a rewritable read only memory or the like such as a flash memory or the like as a storing section, and the image transmitting unit 27 for transmitting the image signals outputted from the imaging panel 23 are provided. Further, the signal receiving unit 28 for receiving a switching signal or an image generation starting signal transmitted from outside, and the switching section for performing a switching operation between an image generation standby mode and an image generation mode based on the switching signal or the image generation starting signal received by the signal receiving unit 28 are also provided.

Therefore, in the control unit 24, by receiving the switching signal or the image generation starting signal transmitted from the console 3 through the signal receiving unit 28, the switching section 29 is activated for switching between the image generation standby mode and the image generation mode. Further, the driving circuit is activated for reading out an electric signal from the photoelectric conversion layer 23, the read electric signal is stored in the image storing unit 26 as an image signal, and then the image signal is transmitted to the console 3 through the image transmitting unit 27. Thereby, the control unit 24 controls each of various types of operations performed in the radiation image detector 1.

Figure 4:
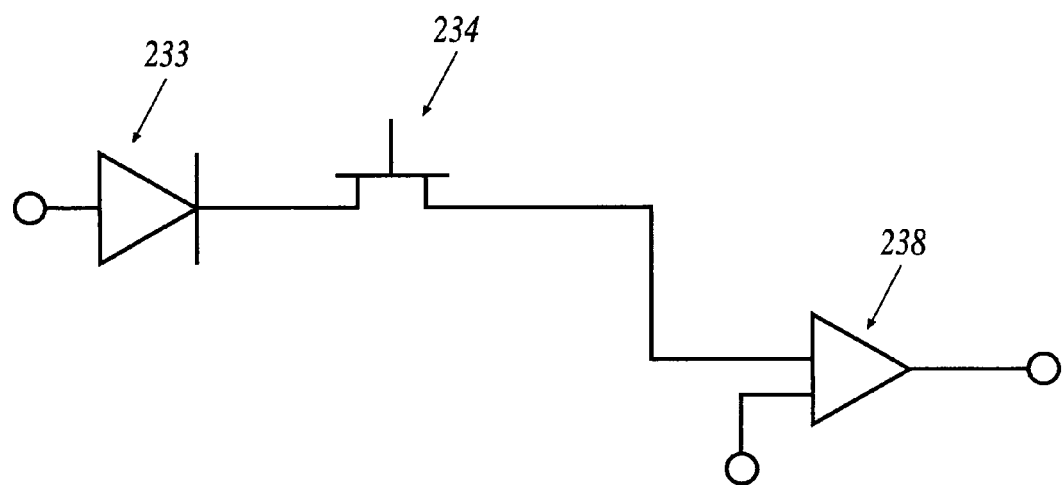
FIG. 4 is a portion of an equivalent circuit structure diagram showing a photoelectric conversion unit structuring a photoelectric conversion layer, corresponding to a one pixel portion.

Here, a circuit structure of the imaging panel 23 will be described. FIG. 4 is an equivalent circuit structure diagram showing a photoelectric conversion unit structuring a photoelectric conversion layer, corresponding to a one pixel portion.

As shown in FIG. 4, the structure of the photoelectric conversion unit corresponding to a one pixel portion is so structured as to comprise the PD 233 and the TFT 234 for taking out the electrical energy accumulated in the PD 233 as an electric signal by the switching. An amplifier 238 amplifies the taken-out electric signal up to a level at which the signal reading circuit 237 is able to detect the signal. Here, a reset circuit (not shown) comprising the TFT 234 and a condenser are connected to the amplifier 238, and the reset circuit performs a reset operation for resetting the accumulated electric signal by turning on the switch of the TFT 234. Further, the PD 233 may be one simply comprising a parasitic capacitance, or one in which additional condensers are arranged in parallel so as to modify a dynamic range of the PD 233 and the photoelectric conversion unit.

Figure 5:
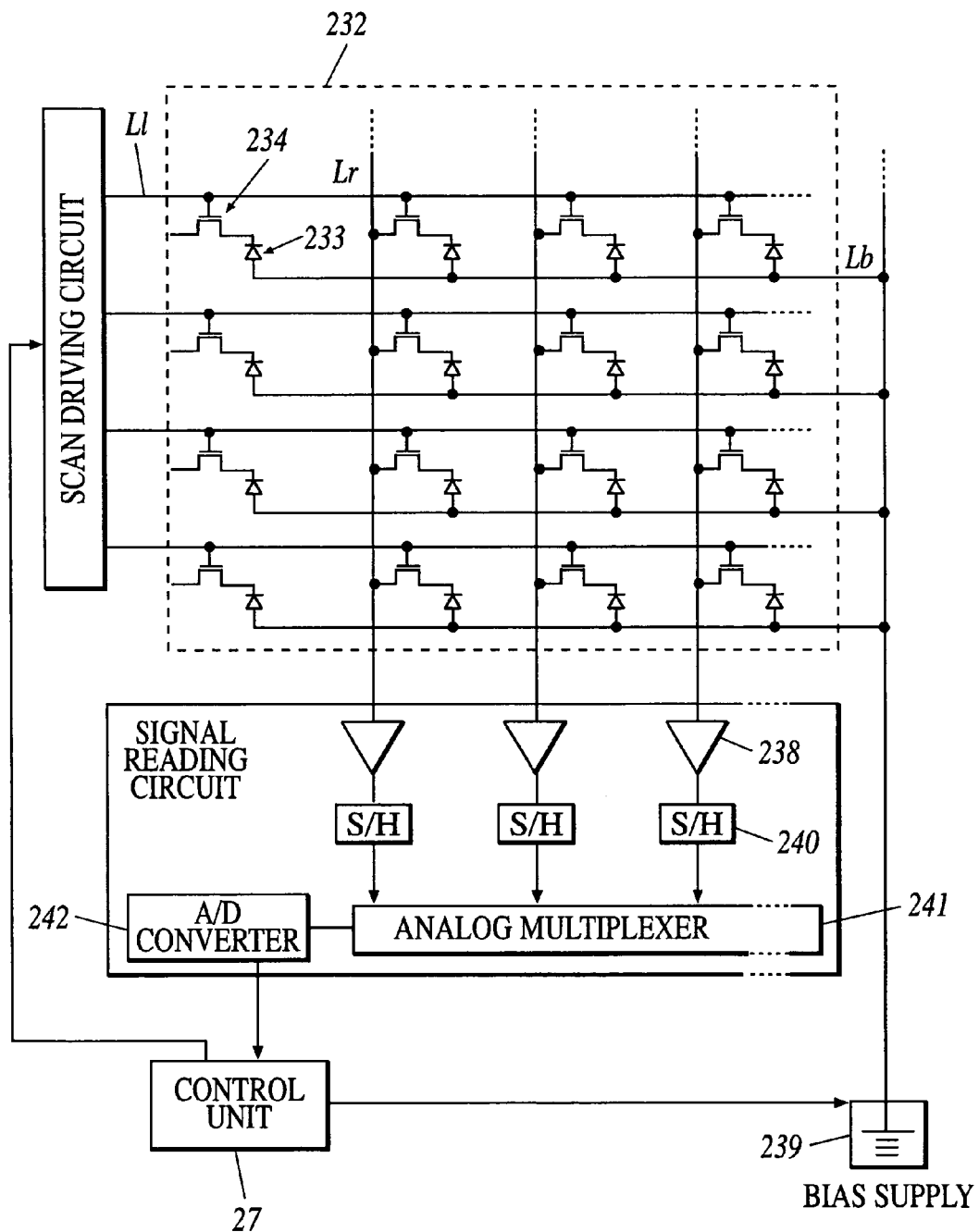
FIG. 5 is a diagram showing an equivalent circuit structure in which the photoelectric conversion units of FIG. 3 are arranged two-dimensionally.

FIG. 5 is a view showing an equivalent circuit in which such electric conversion units are arranged two-dimensionally, and between pixels, a scan line Ll and a signal line Lr are arranged to be orthogonal to each other. The TFT 234 is connected to the above-mentioned PD 233, and an end of the PD 233 to which the TFT 234 is connected is connected to the signal line Lr. On the other hand, another end of the PD 233 is connected to ends of adjacent PD 233 arranged in each line and connected to a bias supply 239 through a common bias line Lb. An end of the bias supply 239 is connected to the control unit 24, and a voltage is applied to the PD 233 through the bias line Lb according to an instruction from the control unit 24. Further, the TFTs 234 arranged in each row are connected to a common scan line Ll, and the Ll is connected to the control unit 24 through the scan driving circuit 236. Similarly, the PDs 233 arranged in each column are connected to a common signal line Lr and connected to the signal reading circuit 237 controlled by the control unit 24. In the signal reading circuit 237, in the order from the closest to the imaging panel 23, the amplifier 238, a sample hold circuit 240, an analog multiplexer 241 and an A/D converter 242 are arranged on the common signal line Lr.

In the radiation image detector 1 in the present embodiment, ON/OFF of the main power source is performed at one day cycle. For example, the power of the radiation image detector 1 is turned on at a test operation of the radiation source 8, thereafter, the power is kept on while there is a possibility of a visit of a subject such as a patient or the like, and the power is turned off at a completion of the radiation image generation of the day.

Normally, it is rare to regularly perform radiation image generation while the power of the radiation image detector 1 is kept on. Therefore, the radiation image detector 1 comprises a switching section 29 for switching between a state where image radiation is being performed (image generation mode) and a state where the detector 1 is on standby for image generation (image generation standby mode). The control unit 24 controls a switching operation of the switching section 29.

Under the image generation mode, all the components structuring the radiation image detector 1 are functioning. In other words, a voltage is being applied to all the components of the radiation image detector 1, and it is possible to perform a series of image generation operations, which are initializing, irradiating a radiation, reading an electrical signal and transmitting an image signal. Here, at the initializing, the imaging panel 23 performs the reset operation and a test reading operation.

The image generation standby mode comprises two standby modes having less electric power consumption than that of the image generation mode, and the two standby modes are: a first standby mode under which a voltage is being applied to the photoelectric conversion layer 232 for a predetermined period before the image generation mode and remaining residual charge is eliminated; and a second standby mode having less electric power consumption than that of the first standby mode. In other words, the first standby mode is an image generation standby mode in a state where there is a high possibility of immediately performing image generation, and the second standby mode is an image generation standby mode in a state where there is a low possibility of immediately performing image generation.

For example, as shown in FIG. 6, it is possible to configure each mode so that, under the image generation mode, a voltage is being applied to the signal reading circuit 237, the scan driving circuit 236, the PD 233, the TFT 234, the image storing unit 26, the image transmitting unit 27 and the signal receiving unit 28; under the first standby mode, a voltage is not applied to the signal reading circuit 237 at least, and all the components have been started up except for the signal reading circuit 237, which can be immediately started up; and under the second standby mode, a voltage is not applied to the photoelectric conversion unit at least, and only the components relating to storing an image, transmitting an image and receiving a signal from outside, which are the image storing unit 26, the image transmitting unit 27 and the signal receiving unit 28 have been started up.

The above-mentioned image generation standby mode and the image generation mode can be switched by the switching section in the radiation image detector 1. When receiving a switching signal transmitted from the console 3 through the signal receiving unit 28, the control unit 24 makes the switching section 29 switch between the image generation standby modes, and when receiving an image generation starting signal transmitted from the console 3 through the signal receiving unit 28, the control unit 24 makes the switching section 29 switch from the image generation standby mode to the image generation mode. Here, the switching signal comprises a switching signal 1 for switching from the second standby mode to the first standby mode, and a switching signal 2 for switching the first standby mode to the second standby mode.

Under the second standby mode, the switching section 29 regularly checks if the switching signal 1 or the image generation starting signal is received. When the switching signal 1 is received, the switching section 29 switches from the second standby mode to the first standby mode. Further, when the image generating starting signal is received, the switching section 29 switches from the second standby mode to the image generation mode. Here, when the image generation starting signal is received under the second standby mode, a mode is switched to the image generation mode under which a voltage is being applied to all the components. However, in such a case, since a voltage relating to the photoelectric conversion layer and the driving circuit is unstable, preferably initialization is started after a predetermined period has passed.

Meanwhile, under the first standby mode, the switching section 29 regularly checks if the switching signal 2 or the image generation starting signal is received. When the switching signal 2 is received under the first standby mode, the switching section 29 switches from the first standby mode to the second standby mode. Further, when the image generation starting signal is received, the switching section switches from the first standby mode to the image generation mode. Here, when the image generation starting signal is received under the first standby mode, a mode is switched to the image generation mode. However, in such a case, since there is the case that a component such as the PD 233 or the like, which requires more time to stabilize a voltage thereof, is not stabilized, preferably initialization is performed after a predetermined period has passed since a mode is switched to the first standby mode.

Concretely, the switching between the first standby mode and the second standby mode is performed in the following way: when the switching signal is transmitted to the switching section 29 through the signal receiving unit 28, the control unit 24 controls the applying of the voltage to the scan driving circuit 236, the PD 233 and the TFT 234, and the voltage of the bias line Lb, for changing an electric potential relating to the photoelectric conversion layer 232.

Further, the switching from the first standby mode to the image generation mode is performed in the following way: when the image generation starting signal is transmitted to the switching section 29 through the signal receiving unit 28, the control unit 24 applies a voltage to the signal reading circuit 237 and thereafter an image generation operation is performed.

In the image generation operation, first, after the reset operation is performed to the signal reading circuit 237, the test reading operation is performed and a radiation is irradiated, and an electrical signal is generated according to radiation amount and accumulated in the PD 233. Then, when the scan line Ll is selected by the scan driving circuit 236 and the switching is performed to the TFT 234 on the selected scan line L1, the electrical signal accumulated in the PD 233 is conducted and transmitted to the signal reading circuit 237. After the transmitted electrical signal is amplified, the electrical signal is converted into a digital signal. Then, after the control unit 24 temporarily stores the digital signal in the image storing unit 26 as an image signal, the image transmitting unit 27 transmits the image signal to the console 3.

Here, when the main power of the radiation image detector 1 is turned on, a mode is automatically switched to the second standby mode, and a voltage is applied to the image storing unit 26, the image transmitting unit 27 and the signal receiving unit 28.

Next, an operation of the radiation image detector 1 comprising such a switching section 29 will be described.

Figure 7:
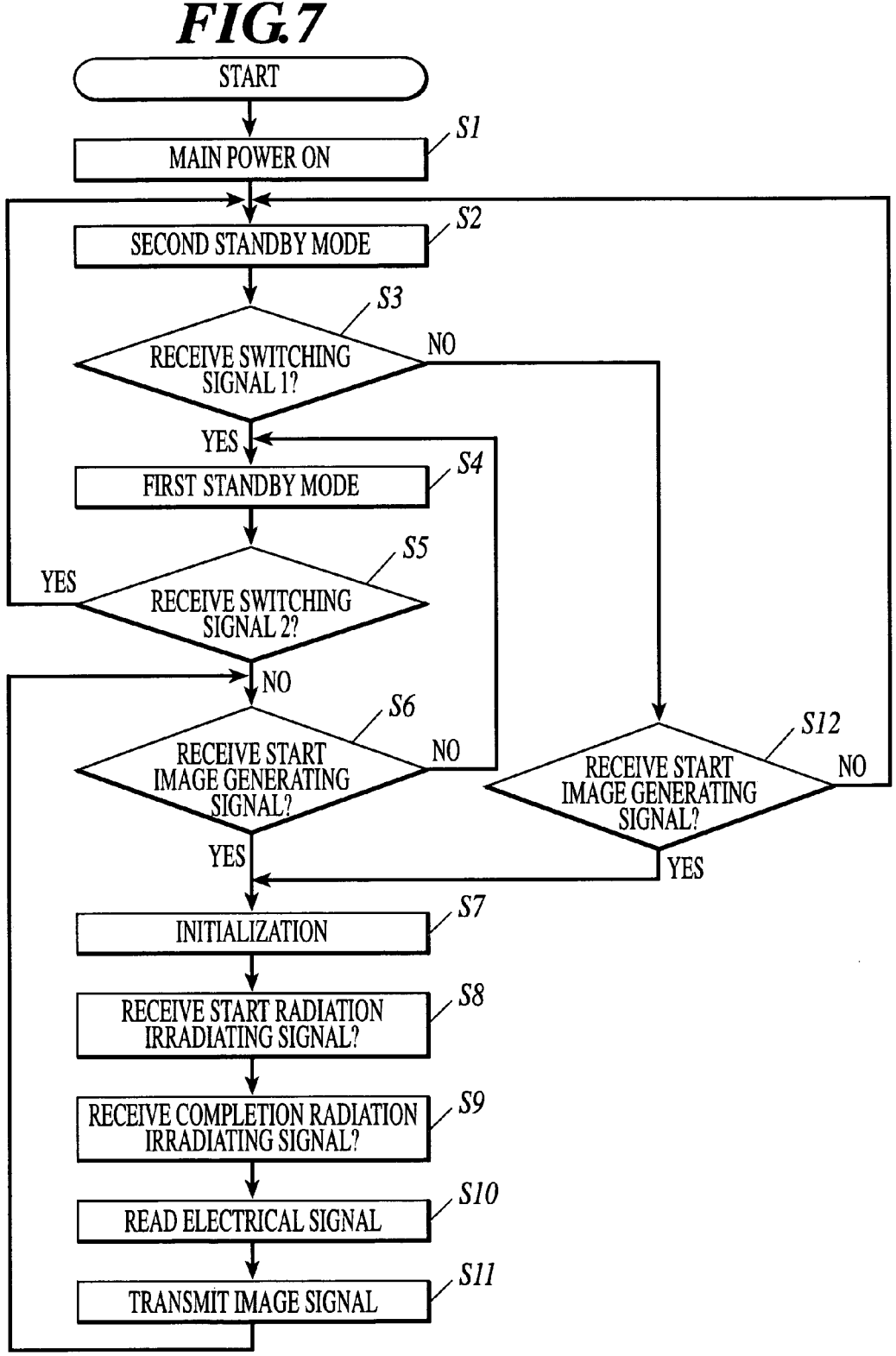
FIG. 7 is a flowchart illustrating an operation flow of the radiation image detector.

As shown in FIG. 7, when the main power of the radiation image detector 1 is turned on (Step S1), a mode is automatically switched to the second standby mode (Step s2).

Under the second standby mode, the image storing unit 26, the image transmitting unit 27 and the signal receiving unit 28 are constantly functioning, and whether the switching signal is received to the signal receiving unit 28 is regularly checked (Step S3).

Then, when the switching signal for switching from the second standby mode to the first standby mode (switching signal 1) is transmitted to the signal receiving unit 28 from the console 3 (Step S3; Yes), the signal receiving unit 28 transmits the signal to the control unit 24. The control unit 24 makes the switching section 29 switch from the second standby mode to the first standby mode, and starts applying a voltage to the scan driving circuit 236 and the reset circuit in the signal reading circuit 237. Then, by applying the voltage to the scan driving circuit 236, the voltage is applied to the PD 233 portion and the TFT 234 portion, and a dark current of the photoelectric conversion unit is gradually stabilized to a stationary state (Step S4).

At this time, the signal receiving unit 28 regularly checks if the switching signal for switching from the first standby mode to the second standby mode (switching signal 2) is received (Step S5).

Then, when it is confirmed that the switching signal 2 is not received (Step S5; No), the signal receiving unit 28 checks if the image generation starting signal transmitted according to an instruction of an operator from the console 3 is received (Step S6).

When it is confirmed that the image generation starting signal is received (Step S6; Yes), after the reset operation and the test reading operation (initialization) are performed (Step S7), the signal receiving unit 28 receives a start radiation irradiating signal (Step S8), and a radiation is irradiated. Then, when the irradiation of the radiation is completed, the signal receiving unit 28 receives a completion radiation irradiating signal (Step. S9), the electrical signal is read according to the driving of the driving circuit (Step S10), and the read image signal is stored and transmitted to the console 3 (Step S11).

Then, after a predetermined period has passed since the image signal is transmitted, the signal receiving unit 28 checks if the image generation starting signal is received, again (Step S6).

When the image generation starting signal is received (step S6; Yes), the image generation operation is performed again, and the operations after Step S7 are repeated.

On the other hand, when the reception of the start image generating signal is not confirmed (Step S6; No), a mode is switched to the first standby mode, and the operations after Step S4 are repeated.

Here, when the reception of the switching signal 2 is not confirmed in Step S5 (Step S5), a mode is switched to the second standby mode, and the operations after Step S2 are repeated.

Further, when the reception of the switching signal 1 is not confirmed in Step S3, whether the start image generating signal is received is checked (Step S12).

When the start image generating signal is received (Step S12; Yes), the image generation operation is performed again, and the operations after Step S7 are repeated.

On the other hand, when the reception of the start image generating signal is not confirmed (Step 12; No), a mode is switched to the second standby mode, and the operations after Step S2 are repeated.

As above, the radiation image detector 1 in the present embodiment comprises the two image generation standby modes (first standby mode and second standby mode) having different electric power consumption from each other, and by making the switching section 29 switch between these modes, it is possible to further reduce electric power consumption amount under an image generation standby mode, and thereby electric power saving is realized.

At this time, under the first standby mode, a voltage is applied to all the components except the signal reading circuit, which does not require too much time to be stabilized and consumes the largest amount of electric power among all. Therefore, it is possible to immediately switch a mode to the image generation mode for immediately starting the image generation, and it is possible to reduce electric power consumption.

Further, under the second standby mode, a voltage is not for a long time applied to the photoelectric conversion layer 232. Therefore, it is possible to prevent the deterioration of the photoelectric conversion layer 232, and thereby it is possible to realize a long life duration of the radiation image detector 1.

Accordingly, in the radiation image generating system 100, it is possible to reduce electric power consumption under an image generation standby mode while an image generation is immediately performed, and it is possible to realize electric power saving and a long life duration thereof.

Here, in the present embodiment, the switching section 29 performs the switching according to the switching signal and the image generation starting signal outputted from the console 3. However, these signals may be outputted from a component provided with the radiation image detector 1 for performing the switching. In this case, for example, the switching section 29 may be actuated according to a signal outputted from a mechanical switch, timer, sensor or the like provided in the radiation image detector 1, the signal from which it is possible to tell the timing to switch between the image generation standby mode and the image generation mode.

In the case of using the mechanical switch, according to an operation by an image generation technician, a signal for switching from the image generation standby mode having low electric power consumption to the image generation standby mode having high electric power consumption, a signal for switching the image generation standby mode having high electric power consumption to the image generation standby mode having low electric power consumption, and a signal for switching from the image generation standby mode to the image generation mode are transmitted to the switching section.

In the case of using the timer, preferably the timer is used with another signal outputting member. For example, after a predetermined time has passed since an image generation instruction is outputted from the operating unit 10, a signal for switching the image generation standby mode having low electric power consumption to the image generation standby mode having high electric power consumption is transmitted to the switching section, then, after a predetermined time has passed since an image signal is transmitted to the console 3, a signal for switching the image generation standby mode having high electric power consumption to the image generation standby mode having low electric power consumption is transmitted to the switching section.

As the sensor, concretely, an acceleration sensor, a thermal sensor, an optical sensor, a pressure sensor, an electric sensor or the like can be used.

In the case of using the acceleration sensor, the acceleration sensor detects an acceleration change of a movement of the radiation image detector 1 when the radiation image detector 1 is taken away from a battery charger to which the radiation image 1 is attached on standby for image generation. When acceleration having not less than predetermined amount is being detected for a predetermined time, the acceleration sensor transmits the signal for switching from the image generation standby mode having low electric power consumption to the image generation standby mode having high electric power consumption, to the switching section. When acceleration having not more than predetermined amount is being detected for a predetermined time, the acceleration sensor transmits the signal for switching from the image generation standby mode having high electric power consumption to the image generation standby mode having low electric power consumption, to the switching section.

In the case of using the thermal sensor, the thermal sensor detects heat of a subject when the subject comes close to the radiation image detector 1. When heat having not less than predetermined temperature is being detected for a predetermined time, the thermal sensor transmits the signal for switching from the image generation standby mode having low electric power consumption to the image generation standby mode having high electric power consumption, to the switching section. When heat having not more than predetermined temperature is being detected for a predetermined time, the thermal sensor transmits the signal for switching from the image generation standby mode having high electric power consumption to the image generation standby mode having low electric power consumption, to the switching section. At this time, as a means for detecting heat, for example, an optical sensor which detects heat by irradiating light such as infrared ray or the like, can be used.

In the case of using the optical sensor, the optical sensor detects a radiation irradiated to the radiation image detector 1. When a radiation having not less than predetermined dose is being detected for a predetermined time, the optical sensor transmits the signal for switching from the image generation standby mode having high electric power consumption to the image generation standby mode having low electric power consumption, to the switching section. When a radiation having not more than predetermined dose is being detected for a predetermined time, the optical sensor transmits the signal for switching from the image generation standby mode having low electric power consumption to the image generation standby mode having high electric power consumption, to the switching section.

In the case of using the pressure sensor, the pressure sensor detects pressure as to when a subject is contacted with the radiation image detector 1. When pressure having not less than predetermined amount is being detected for a predetermined time, the pressure sensor transmits the signal for switching from the image generation standby mode having high electric power consumption to the image generation standby mode having low electric power consumption, to the switching section. When pressure having not more than predetermined amount is being detected for a predetermined time, the pressure sensor transmits the signal for switching from the image generation standby mode having low electric power consumption to the image generation standby mode having high electric power consumption, to the switching section.

In the case of using the electrical sensor, the electrical sensor detects a change of electrical energy of the radiation image detector 1, for example, the electrical sensor detects a change of a voltage that is applied from a battery charger to which the radiation image detector 1 is attached on standby for image generation. In this case, when the electrical sensor detects from the fact that the radiation image detector 1 is taken away from the battery charger and a voltage is not applied to the radiation image detector 1, the electrical sensor transmits the signal for switching from the image generation standby mode having low electric power consumption to the image generation standby mode having high electric power consumption, to the switching section. When the radiation image detector 1 is again attached to the battery charger and a voltage is applied thereto, the electrical sensor transmits the signal for switching from the image generation standby mode having high electric power consumption to the image generation standby mode having low electric power consumption, to the switching section.

Further, in the present embodiment, a communication between the radiation image detector 1 and the console 3 is performed according to a wireless communication system. However, by providing a transmittance terminal with both of the radiation image detector 1 and the console 3, and by directly connecting these transmittance terminals, image data obtained in the radiation image detector 1 may be transmitted. In this case, since it is not a wireless communication system, image data does not get lost during the transmittance due to a cutoff of an electric wave during the communication, and thereby it is possible to transmit data easily and reliably.

Further, instead of storing obtained data in the image storing unit 26 of the radiation image detector 1, image data obtained in the radiation image detector 1 may be transmitted with a memory attaching unit in the following way: a detachable memory is attached to the memory attaching unit, and after the entire image data is stored therein, the memory is attached to the memory attaching unit of the console 3 side to transfer the image data. In this case also, since it is not a wireless communication system, image data does not get lost during the transmittance due to a cutoff of an electric wave during the communication, and thereby it is possible to transmit data easily and reliably.

Second Embodiment

Next, a different pattern of an image generation standby mode relating to the present invention will be described. In the present embodiment, a second pattern will be described in the following. However, descriptions of parts identical to the first embodiment will be omitted.

This pattern is also a case having two image generation standby modes, with a nonvolatile memory used as a memory thereof. As shown in FIG. 8, when a possibility of immediately performing image generation is low, the system is on standby under a second standby mode under which only the signal receiving unit 28, which relates to a signal reception from outside, has been started up, and when the possibility of immediately performing image generation is high, the system is on standby under a first standby mode under which a voltage is applied to the PD 233, which requires the largest amount of time to be stabilized since the startup under the second standby mode.

With this pattern, since the number of components which have been started up under the first standby mode and under the second standby mode is fewer than that of the first pattern, it is possible to further reduce electric power consumption than the first pattern. Further, since a nonvolatile memory is used, it is possible to turn off the main power of the radiation image detector while it is not necessary to use the memory.

Third Embodiment

Next, as a different pattern of an image generation standby mode relating to the present invention, a third pattern will be described hereafter. However, descriptions of parts identical to the first embodiment will be omitted.

This pattern is also a case having two image generation standby modes, with a volatile memory used as a memory thereof. As shown in FIG. 9, when a possibility of immediately performing image generation is low, the system is on standby under a second standby mode under which only the signal receiving unit 28, which relates to a signal reception from outside, has been started up, and when the possibility of immediately performing image generation is high, the system is on standby under a first standby mode under which a voltage is applied to the PD 233, which requires the largest amount of time to be stabilized since the startup under the second standby mode.

Also with this pattern, since the number of components which have been started up under the first standby mode and under the second standby mode is fewer than that of the first pattern, it is possible to further reduce electric power consumption than the first pattern. However, since a volatile memory is used, it is not possible to turn off the main power of the radiation image detector, whereby electric power consumption thereof is larger than the second pattern.

Fourth Embodiment

Next, Next, as another pattern of an image generation standby mode relating to the present invention, a fourth pattern will be described hereafter. However, descriptions of parts identical to the first embodiment will be omitted.

This pattern is a case having three image generation standby modes. The case having three image generation standby modes uses a volatile memory as its memory. In the present embodiment, a component which requires larger amount of time to be stabilized is started up under an earlier step of the standby mode. As shown in FIG. 10, under a third standby mode, which is arranged when a possibility of immediately performing image generation is low, the system is on standby so that only the signal receiving unit 28, which relates to a signal reception from outside, has been started up. Thereafter, under a second standby mode, a voltage is further applied to the PD 233, which requires the largest amount of time to be stabilized since the startup, under the third standby mode. Thereafter, the system is on standby under a first standby mode under which a voltage is further applied to the TFT 234 and the scan driving circuit under the state of the second standby mode.

With this pattern, since it is possible to increase image generation standby modes having different electric power consumption amount from each other compared to the first pattern, it is possible to further reduce electric power consumption.

Fifth Embodiment

Next, as another pattern of an image generation standby mode relating to the present invention, a fifth pattern will be described hereafter. However, descriptions of parts identical to the first embodiment will be omitted.

This pattern is a case having not less than two image generation standby modes, and the switching of the standby modes by the switching section 29 is different between before the image generation mode and after the image generation mode.

Before the image generation, since the switching from the standby mode to the image generation mode is required to be done as soon as possible, as shown in FIG. 11, when a possibility of immediately performing image generation is low, the system is on standby under a third standby mode under which only the signal receiving unit 28, which relates to a signal reception from outside, has been started up, and under a first standby mode before the image generation mode, all the components that are necessary to be stabilized are started up.

On the other hand, after the image generation, the applying of a voltage to components which requires small amount of time to be stabilized is discontinued. However, since there is a possibility of receiving a next image generation request, the system comprises a second standby mode under which a voltage is applied not only to the signal receiving unit 28 but also to the PD 233, which requires the most amount of time to be stabilized.

With this pattern, it is possible to further reduce electric power consumption than the first pattern, and it is possible to immediately re-perform image generation.

The entire disclosure of a Japanese Patent Application No. 2005-23823, filed on Jan. 31, 2005, including the specification, claims, drawings and summaries are incorporated herein by reference in their entirety.

What is claimed is:

1. A radiation image detector for detecting an irradiated radiation and for obtaining radiation image information, the radiation image detector comprising:
an image generation mode; and
a plurality of image generation standby modes,
wherein the plurality of image generation standby modes comprises:
a first standby mode having electric power consumption amount at least lower than electric power consumption amount of the image generation mode; and
a second standby mode having electric power consumption amount lower than the electric power consumption amount of the first standby mode, and
the radiation image detector comprises a switching section for switching among the image generation mode and the plurality of image generation standby modes.

2. The detector of claim 1, further comprising:
a signal reading circuit;
a scan driving circuit;
a photoelectric conversion unit;
an image storing unit;
an image transmitting unit; and
a signal receiving unit,
wherein the switching section does not apply a voltage to at least the signal reading circuit under the first standby mode.

3. The detector of claim 2, wherein the switching section does not apply a voltage to at least the photoelectric conversion unit under the second standby mode.

4. The detector of claim 1, wherein the switching section switches among the image generation mode and the plurality of image generation standby modes, according to one of: a signal from a mechanical switch; a signal from outside; and a signal from a sensor.

5. The detector of claim 4, wherein the sensor is at least one selected from a group consisting of:
an acceleration sensor for detecting a movement;
a thermal sensor for detecting heat;
an optical sensor for detecting a light;
a pressure sensor for detecting a pressure; and
an electric sensor for detecting electric energy.

6. The detector of claim 1, further comprising a wireless communication unit for communicating with a wireless signal.

7. The detector of claim 1, wherein the detector is a cassette type radiation image detector contained in a cassette.

8. The detector of claim 1, further comprising a battery as an electric power supplying source.

9. A radiation image generating system comprising:
the radiation image detector of claim 1; and
a console for operating the radiation image detector.

* * * * *